United States Patent
Menges et al.

(10) Patent No.: US 8,563,734 B2
(45) Date of Patent: *Oct. 22, 2013

(54) 2-[1-CYANOPROPYL)CARBAMOYL]-5-CHLOROMETHYL NICOTINIC ACIDS AND THE USE THEREOF IN MANUFACTURING HERBICIDAL IMIDAZOLINONES

(75) Inventors: Frederik Menges, Schriesheim (DE); Joachim Gebhardt, Wachenheim (DE); Michael Rack, Eppelheim (DE); Michael Keil, Freinsheim (DE); Rodney F. Klima, Quincy, IL (US); David Cortes, Quincy, IL (US); Robert Leicht, Hannibal, MO (US); Helmut Zech, Bad Duerkheim (DE); Jochen Schröder, Lambsheim (DE)

(73) Assignee: BASF SE, Ludwigshafen (DE)

( * ) Notice: Subject to any disclaimer, the term of this patent is extended or adjusted under 35 U.S.C. 154(b) by 344 days.

This patent is subject to a terminal disclaimer.

(21) Appl. No.: 13/128,782

(22) PCT Filed: Nov. 3, 2009

(86) PCT No.: PCT/EP2009/064495
§ 371 (c)(1),
(2), (4) Date: May 11, 2011

(87) PCT Pub. No.: WO2010/054952
PCT Pub. Date: May 20, 2010

(65) Prior Publication Data
US 2011/0218340 A1    Sep. 8, 2011

Related U.S. Application Data

(60) Provisional application No. 61/114,238, filed on Nov. 13, 2008.

(51) Int. Cl.
C07D 401/04    (2006.01)
C07D 211/78    (2006.01)

(52) U.S. Cl.
USPC ........................ 546/274.1; 546/318

(58) Field of Classification Search
USPC .............................. 546/274.1, 318
See application file for complete search history.

(56) References Cited

U.S. PATENT DOCUMENTS

| | | | |
|---|---|---|---|
| 5,026,859 A | 6/1991 | Finn | |
| 5,334,576 A | 8/1994 | Doehner, Jr. et al. | |
| 5,378,843 A | 1/1995 | Strong | |
| 5,760,239 A | 6/1998 | Wu | |

FOREIGN PATENT DOCUMENTS

| | | |
|---|---|---|
| DE | 3330604 | 3/1985 |
| EP | 0144595 | 6/1985 |
| EP | 0184027 | 6/1986 |
| EP | 0322616 | 7/1989 |
| EP | 0 539 676 | 5/1993 |
| EP | 0 548 532 | 6/1993 |
| EP | 0747360 | 12/1996 |
| EP | 0933362 | 4/2002 |
| WO | WO 2010/054954 | 5/2010 |
| WO | WO 2010/055042 | 5/2010 |
| WO | WO 2010/055139 | 5/2010 |
| WO | WO 2010/006668 | 6/2010 |

OTHER PUBLICATIONS

Tagawa, Y. et al., "Reinvestigation of nitrosation of methlypyridines and their 1-oxides and deoxygenation of 3-pyridinecarbaldehyde 1-oxide oxime", Heterocycles, (1992), pp. 1605-1612, vol. 34, No. 8.
Zubrik, James. W., "The Organic Chem Lab Survival Guide", copyright 1984, 1988, by John Wiley & Sons, Inc.
Office Action dated Sep. 17, 2012, in U.S. Appl. No. 13/128,779, filed May 11, 2011.
Bi, Q. et al., "Review on Synthesis of Imazamox", Modern Agrochemicals, vol. 6, No. 2, (2007), pp. 10-14.
International Preliminary Report on Patentability, issued in PCT/EP2009/064495, dated May 26, 2011.
International Search Report, issued in PCT/EP2009/064495, dated Dec. 29, 2009.

*Primary Examiner* — Nizal Chandrakumar
(74) *Attorney, Agent, or Firm* — Brinks Hofer Gilson & Lione

(57) ABSTRACT

2-[(1-cyanopropyl)carbamoyl]-5-chloromethyl nicotinic acids of formula (I) where Z is hydrogen or halogen; $Z^1$ is hydrogen, halogen, cyano or nitro; $R^1$ is $C_1$-$C_4$ alkyl; $R^2$ is $C_1$-$C_4$ alkyl, $C_3$-$C_6$ cycloalkyl or $R^1$ and $R^2$, when taken together with the atom to which they are attached, represent a $C_3$-$C_6$ cycloalkyl group optionally substituted with methyl, and $R^3$ is hydrogen or a cation preferably selected from the group consisting of alkali metals, alkaline earth metals, manganese, copper, iron, zinc, cobalt, lead, silver, nickel, ammonium and organic ammonium; are useful intermediates for the synthesis of herbicidal imidazolinones.

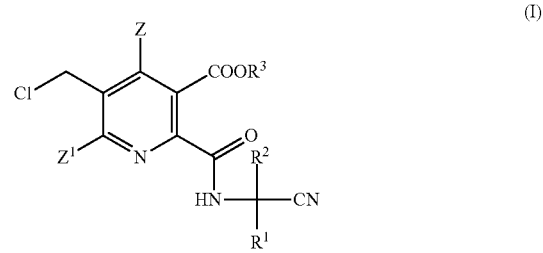

(I)

14 Claims, No Drawings

2-[1-CYANOPROPYL)CARBAMOYL]-5-CHLOROMETHYL NICOTINIC ACIDS AND THE USE THEREOF IN MANUFACTURING HERBICIDAL IMIDAZOLINONES

This application is a National Stage application of International Application No. PCT/EP2009/064495, filed Nov. 3, 2009, which claims the benefit of U.S. Provisional Application No. 61/114,238, filed Nov. 13, 2008, the entire contents of which are hereby incorporated herein by reference.

The invention relates to 2-[(1-cyanopropyl)carbamoyl]-5-chloromethyl nicotinic acids, the preparation of these compounds and their use in manufacturing herbicidal imidazolinones, such as imazamox.

Derivatives of 2-(2-imidazolin-2-yl)nicotinic acids, like imazamox (2-[(RS)-4-isopropyl-4-methyl-5-oxo-2-imidazolin-2-yl]-5-methoxymethyl nicotinic acid),

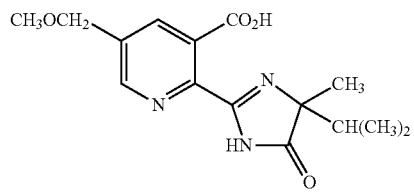

are useful selective herbicides which act as ALS-inhibitors and can be used in pre- and post-emergence applications.

Various processes for the synthesis of these compounds are known from the literature, see e.g. EP-A 0 322 616, EP-A 0 747 360, EP-A 0 933 362 or Q. Bi et al, Modern Agrochemicals 6(2)(2007) 10-14.

Although synthesis on an industrial scale is carried out by these methods there is still room for improvement, specifically in view of economical and ecological aspects, such as overall yield improvement or the avoidance of certain solvents or reagents.

EP-A 0 322 616 discloses the synthesis of 2-[(1-carbamoyl-1,2-dimethylpropyl)carbamoyl]-5-chloromethyl nicotinic acid by reaction of 5-chloromethyl-2,3-pyridine dicarboxylic acid anhydride with α-amino-α-methylvaleramide and further conversion of this compound to imazamox by reaction with $NaOCH_3$ and subsequent acidification.

One task of the invention is to provide new useful intermediates for the synthesis of herbicidal imidazolinones, and a process for their preparation. A further task of the invention is to provide an improved process for manufacturing herbicidal imidazolinones, like imazamox.

It has been found that 2-[(1-cyanopropyl)carbamoyl]-5-chloromethyl nicotinic acids are useful intermediates in the manufacture of herbicidal imidazolinones.

EP-A 0 184 027 and EP-A 0 144 595 describe the reaction of pyridine-2,3-dicarboxylic acid anhydrides with 2-amino-2,3-dimethyl-butyronitrile and further conversion to herbicidal imidazolinones, however, no examples for 5-chloromethyl substituted compounds are disclosed.

Accordingly, in one aspect of the invention there is provided a 2-[(1-cyanopropyl)carbamoyl]-5-chloromethyl nicotinic acid of formula (I),

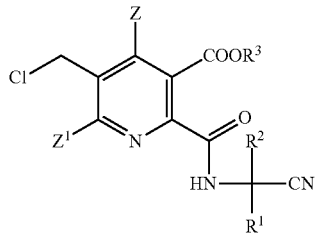

where
Z is hydrogen or halogen;
$Z^1$ is hydrogen, halogen, cyano or nitro;
$R^1$ is $C_1$-$C_4$ alkyl;
$R^2$ is $C_1$-$C_4$ alkyl, $C_3$-$C_6$ cycloalkyl or $R^1$ and $R^2$, when taken together with the atom to which they are attached, represent a $C_3$-$C_6$ cycloalkyl group optionally substituted with methyl, and
$R^3$ is hydrogen or a cation preferably selected from the group consisting of alkali metals, alkaline earth metals, manganese, copper, iron, zinc, cobalt, lead, silver, nickel, ammonium and organic ammonium.

In another aspect of the invention there is provided a process for preparing a 2-[(1-cyanopropyl)carbamoyl]-5-chloromethyl nicotinic acid of formula (I), comprising the step of
(i) reacting a 5-chloromethyl-pyridine-2,3-dicarboxylic acid anhydride of formula (II),

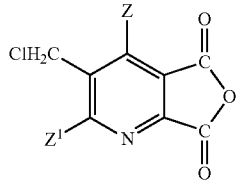

where Z, $Z^1$ are as in formula (I),
with a 2-aminoalkane carbonitrile (III),

where $R^1$ and $R^2$ are as in formula (I).

In a further aspect of the invention there is provided the use of a compound of formula (I) for preparing a herbicidal imidazolinone of formula (IV),

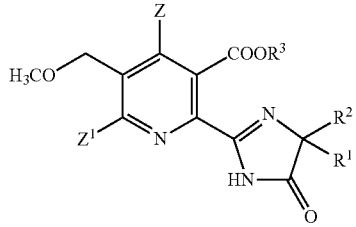

wherein
Z, $Z^1$, $R^1$, $R^2$, $R^3$ are as defined in formula (I).

In a further aspect of the invention there is provided a process for preparing a herbicidal imidazolinone compound of formula (IV), comprising the steps of:
(i) hydrolyzing the nitrile of formula (I) to obtain an amide of formula (V),

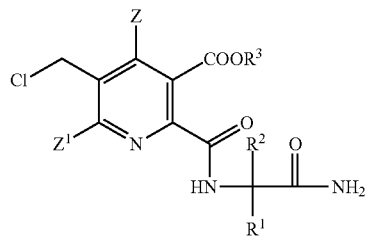

(V)

where

Z, $Z^1$, $R^1$, $R^2$, $R^3$ are as defined in formula (I); and (ii) reacting compound (V) with $CH_3OM$ or $MOH/CH_3OH$ (where M is alkali metal, preferably Na or K), optionally followed by acidification to form the herbicidal imidazolinone (IV).

The use of the novel intermediate (I) in the synthesis of herbicidal imidazolinones leads to an improved yield in preparing amide (V) and, thus, in the overall yield of the synthetic process. The regioselectivity of the opening of the anhydride is excellent even without the addition of the nitrogen bases recommended in EP-A 0 144 595.

In formula (I) the symbols preferably have the following meanings:

Z is preferably hydrogen.

$Z^1$ is preferably hydrogen.

$R^1$ is preferably $C_1$-$C_4$ alkyl.

$R^2$ is preferably $C_1$-$C_4$ alkyl.

$R^3$ is preferably hydrogen, alkali metal or $NR^4R^5{}_3$, where $R^4$ is hydrogen or $R^5$, and $R^5$ is $C_1$-$C_4$ alkyl.

Preferred are compounds of formula (I) where all symbols have the preferred meanings.

A particularly preferred compound of formula (I) is compound (Ia):

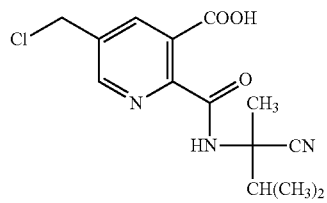

(Ia)

and salts thereof.

Compound (I) can be prepared by reaction of anhydride (II) with aminonitrile (III) as exemplified by the synthesis of preferred compound (Ia), where $R^1$ and $R^2$ are defined as in formula (III):

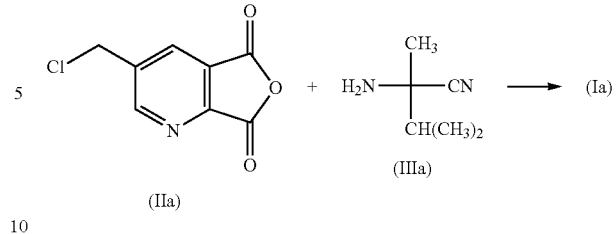

Aminonitriles (III) are commercially available or can be prepared by methods known in the art. Generally 0.8 to 1.2 equivalents aminonitrile (III) per equivalent of compound (II) are used, preferably 0.95 to 1.1.

The reaction is carried out in a solvent, which is preferably selected from aromatic hydrocarbons, preferably toluene, mesitylenes, chlorinated aromatic hydrocarbons, such as chlorobenzene, dichlorobenzenes, chlorinated aliphatic hydrocarbons, such as 1,2-dichloroethane and dichloromethane, acetic acid, and mixtures thereof.

If acetic acid is not used as the main solvent, addition of 0.5 to 10 equivalents, preferably 1 to 3 equivalents (based on compound (II)), is advantageous.

Further advantageous additives that improve the selectivity of the ring-opening reaction (2 versus 3 position) are listed in U.S. Pat. No. 4,562,257, and comprise pyridine, 4-picoline, 2-picoline and quinoline. However, although these additives can be used, according to the invention it is not necessary to employ such additives, and in one embodiment, the listed additives are not present in the reaction mixture.

The reaction is generally carried out at a temperature range of from about 40 to about 120° C., preferably of from about 60 to about 100° C. The reaction time is generally from about 1 to about 3 h.

In a preferred embodiment compound (II) is dissolved in the solvent and brought to the reaction temperature, and aminonitrile (III) is gradually added. After completion of the reaction and cooling, nitrile compound (I) can be isolated by standard methods.

In a further preferred embodiment, however, compound (I) is not isolated but the reaction mixture is directly used for the following hydrolyzation of the nitrile.

In a preferred embodiment of the invention the anhydride (II) that is used in the preparation of compound (I) is obtained by a process comprising the steps of (i) reacting a compound of formula (VI),

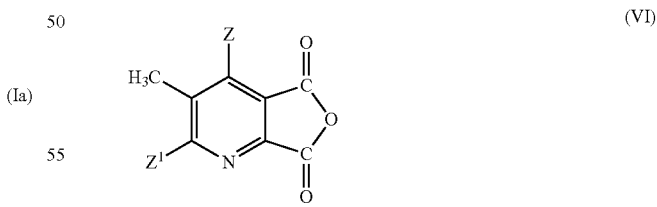

(VI)

wherein the symbols have the meaning given in formula (I), with a chlorinating agent, optionally in the presence of a radical initiator in a solvent selected from halogenated hydrocarbons, preferably from dichloroethane, chlorobenzene, 1,2-dichlorobenzene, 1,3-dichlorobenzene, 1,4-dichlorobenzene and tetrachloromethane, and (ii) crystallization of the compound (II) formed in step (i) from a solvent selected from 1,2-dichloroethane, chlorobenzene, 1,2-dichlorobenzene, 1,3-dichlorobenzene, 1,4-dichlorobenzene, trichloromethane, dichloromethane, toluene, xylenes, mesitylenes, alkyl acetates (e.g. ethyl acetate, butyl acetate, methyl acetate), methyl tert.-butyl ether, diisopropylether, cyclopentyl methyl ether, and mixtures thereof.

Compounds of formula (V) and their preparation are known, e.g. from EP-A 0 933 362.

Suitable chlorinating agents include chlorine, sulfurylchloride, N-chlorosuccinimide, and trichloroisocyanuric acid. Preferred chlorinating agents are chlorine and sulfurylchloride ($SO_2Cl_2$).

The molar ratio of pyridine compound (VI) to chlorinating agent is generally in the range of 1:0.5-1.5, preferably 1:0.7-1.2, more preferably 1:0.8-1.1.

Suitable free-radical generators for initiating the reaction are those which decompose at the selected reaction temperature, i.e. both those which decompose by themselves and those which do so in the presence of a redox system. Examples of preferred initiators are free-radical generators, such as azo compounds and peroxides. It is also possible, however, to use redox systems, especially those based on hydroperoxides, such as cumene hydroperoxide. Light induced chlorination without addition of an initiator is also possible.

Radical initiators suitable for use in the method of the invention include 2,2'-azobisisobutyronitrile (AIBN), 2,2'-azobis(2-methylbutyronitrile), 2,2'-azobis(2,4-dimethylpentanenitrile), 1,1'-azobis(cyclohexanecarbonitrile), organic and inorganic peroxides such as dilauroyl peroxide, hydrogen peroxide, benzoyl peroxide and the like, with 2,2'-azobisisobutyronitrile, 2,2'-azobis(2-methylbutyronitrile) and dilauroyl peroxide being preferred, and 2,2'-azobisisobutyronitrile being particularly preferred.

Preferably the initiator is added continuously over the course of the reaction.

The molar ratio of initiator to chlorinating agent is preferably in the range of 0.001-0.1:1, more preferably 0.002-0.05.

Organic solvents for step (i) are halogenated hydrocarbons, preferably chlorinated hydrocarbons, more preferably chlorinated aliphatic or aromatic hydrocarbons. Strongly preferred are solvents selected from chlorobenzene, 1,2-dichlorobenzene, 1,3-dichlorobenzene, 1,4-dichlorobenzene, 1,2-dichloroethane and tetrachloromethane, preferably 1,2-dichlorobenzene, 1,3-dichlorobenzene, 1,4-dichlorobenzene, 1,2-dichloroethane and chlorobenzene. Chlorobenzene is particularly preferred. The term solvent as used herein includes mixtures of two or more of the above compounds. In addition the term comprises solvents that contain up to 20% by weight, preferably up to 10% by weight, in particular up to 5% by weight of further solvents which are not halogenated hydrocarbons.

The amount of organic solvent may vary to a large extent. Preferably 250 g to 1500 g, more preferably 500 g to 1000 g, of organic solvent per mol of compound (V) are employed.

In one preferred embodiment (where the chlorinating agent is a liquid) step (i) is carried out by dissolving compound (VI) in the organic solvent, heating, and slowly adding a solution of the initiator in the chlorinating agent. After completion of the reaction the solvent is partly or completely distilled off, and the mixture is slowly cooled down to precipitate the product.

In a further preferred embodiment compound (VI) is dissolved in the solvent, and gaseous chlorine is charged to the reaction vessel or passed through the solution. After completion of the reaction the solvent is at least partly distilled off to remove excess chlorine and gaseous byproducts such as HCl. The reaction mixture is then cooled down and compound (II) is precipitated.

In a further preferred embodiment reaction (step (i)) is carried out as a continuous operation.

If chlorine is used as chlorinating agent the reaction is generally carried out at a temperature of about 0° C. to about 160° C., preferably about 60° C. to about 140° C., particularly preferred about 80° C. to about 120° C.

If a liquid chlorinating agent is used, in particular sulfurylchloride, the reaction is generally carried out at a temperature of about 0° C. to about 140° C., preferably about 50° C. to about 120° C., particularly preferred about 70° C. to about 90° C.

The reaction may be carried out under atmospheric pressure or under elevated pressure of up to 6 bar, preferably up to 2 bar. Elevated pressure is preferred if chlorine is used as chlorinating agent.

The reaction time (for step (i)) differs with the reaction parameters but is generally between 5 min and 300 h. In case of a continuous reaction the residence time in the reaction vessel is preferably in the range of 2 to 10 minutes, in particular about 5 minutes.

In step (ii) of the reaction compound (II) is crystallized from a solvent selected from chlorobenzene, 1,2-dichlorobenzene, 1,3-dichlorobenzene, 1,4-dichlorobenzene, 1,2-dichloroethane, trichloromethane, toluene, xylenes, mesitylenes, ethyl acetate, butyl acetate, methyl acetate, methyl tert.-butyl ether, diisopropyl ether, cyclohexyl methyl ether, and mixtures thereof.

The term solvent as used herein includes solvent mixtures.

Chlorobenzene and the dichlorobenzenes are preferred, chlorobenzene is particularly preferred.

It is possible that the solvent used for crystallization comprised up to 90% by weight, preferably from 10 to 80% by weight, in particular 20 to 60% by weight of an anti-solvent, i.e. a liquid in which the compound of formula (I) is essentially insoluble, such as aliphatic hydrocarbons, like n-hexane, hexanes, or cyclohexane.

Crystallization is generally carried out at a temperature in the range from about −40° C. to 30° C., preferably about 0° C. to about 20° C. The concentration of compound (I) in the solvent from which it is crystallized is generally in the range of from 5 to 60% by weight, preferably 10 to 50% by weight.

Crystallization can be carried out by standard methods, e.g. by cooling of a saturated solution of compound (II), by seeding with pure compound (I), by adding an anti-solvent, or by a combination of these methods.

According to the invention compound (II) must be at least once crystallized from one of the above listed solvents or a mixture of two or more of these solvents.

In a preferred embodiment of the invention the chlorination of step (i) is carried out in a solvent which can be used for the crystallization of step (ii). Preferably compound (II) is then crystallized from the reaction mixture after the completion of step (i).

Optionally the original solvent may be partially (or completely) distilled off, and it is also possible to add further solvent, e.g. to compensate for solvent that was distilled off.

It is further preferred to recrystallize compound (II) once or more, preferably once, to improve the purity of the product. Recrystallization is usually carried out in the same solvent as the initial solvent, but of course it is also possible to use a different solvent or solvent mixture from the listed group.

The mother liquor of a recrystallization is preferably recycled to the first crystallization step to minimise yield losses.

In a further preferred embodiment of the invention the chlorination of step (i) is carried out in a solvent which is different from the solvents used for the crystallization of step (ii). In this embodiment the solvent of step (i) is removed, and raw compound (I) is dissolved in a solvent of step (ii) and crystallized. One or more re crystallization steps with the same or different solvents are or course possible, and mother liquor can be recycled as stated above.

It is preferred that the same solvent is used in step (i) and (ii), in particular chlorobenzene or dichlorobenzene.

The purity of compound (I) after re crystallization, determined by HPLC (after quench of the analyt with methanol), is preferably at least 95%, more preferably at least 98%.

Isolation of compound (II) after (re) crystallization can be carried out by standard methods, e.g. by filtration, washing with a suitable solvent and drying.

Compound (II) prepared as described above is particularly useful for the synthesis of the inventive intermediate (I) because of its purity. Therefore, in a preferred embodiment the process for preparing compound (I) comprises the steps of
(i-1) reacting a compound of formula (VI),

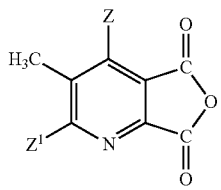

(VI)

wherein the symbols have the meaning given in formula (I), with a chlorinating agent, optionally in the presence of a radical initiator, in a solvent selected from halogenated hydrocarbons, and (i-2) crystallizing the compound (II) formed in step (i) from a solvent selected from 1,2-dichloroethane, chlorobenzene, 1,2-dichlorobenzene, 1,3-dichlorobenzene, 1,4-dichlorobenzene, trichloromethane, dichloromethane, toluene, xylenes, mesitylenes, alkyl acetates (e.g. ethyl acetate, butyl acetate, methyl acetate), methyl tert.-butyl ether, diisopropylether, cyclopentyl methyl ether, and mixtures thereof, to obtain anhydride (II), and (i-3) reacting anhydride (II) with a 2-aminoalkane carbonitrile (III),

$H_2N—CR^1R^2—CN$ (III), where $R^1$ and $R^2$ areas in formula (I).

The compounds of formula (I) are useful intermediates in the synthesis of herbicidal imidazolinones (IV).

In a first step the nitrile function is hydrolyzed to yield the respective amide (V) as exemplified with preferred compounds (Ia) and (Va):

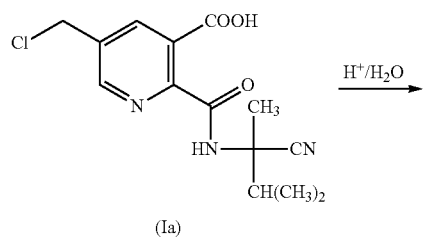

(Ia)

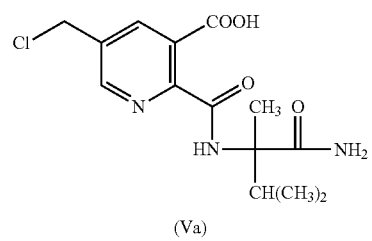

(Va)

In a typical procedure a slight excess (e.g. 1.1 to 1.5 equivalents based on (I)) of a strong mineral acid, preferably sulfuric acid (preferably in a concentration of 30 to 98%) and water (e.g. 2 to 10 equivalents) are added at a temperature which is generally in the range of about 30° C. to 120° C., preferably 50° C. to 90° C. The mixture is further stirred until complete conversion. The reaction time is generally from 1 to 8 h, preferably 1 to 5 h.

Workup and isolation can be achieved by standard methods, such as precipitation from an aqueous solution (e.g. as its ammonium salt). In a preferred embodiment the reaction mixture is directly used in the following reaction step.

In a further process of the invention a herbicidal imidazolinone compound (IV) is prepared by a process comprising the steps of (i) preparing an amido compound of formula (V); and (ii) reacting compound (V) with $CH_3OM$ or $MOH/CH_3OH$ (where M is alkali metal, preferably Na or K) followed by acidification to form the herbicidal imidazolinone (IV).

In one embodiment, in step (ii) amido compound (V), preferably in the form of an ammonium salt ($R^3$ is $HNR_3$), is reacted with an alkali metal methoxide, preferably $NaOCH_3$ in methanol in analogy to example 11 of EP 0 322 616. The resulting suspension is held at reflux until complete conversion. After cooling the mixture is acidified to obtain compound (IV) either as the ammonium salt (acidification to a pH of about 4) or the free acid (acidification to pH≤2).

In a further preferred embodiment, in step (ii) the reaction mixture from step (i) is reacted with methanol (generally 2 to 100 equivalents based on (V)) in the presence of an aqueous base (generally 3 to 100 equivalents based on (V)), the base being preferably selected from MOH and $MOCH_3$, where M is an alkali metal, preferably Na or K, particularly Na.

The reaction is carried out at a temperature in the range of from 20 to 120° C., preferably 40 to 90° C. The reaction can be carried out at atmospheric pressure or at elevated pressure, preferably the pressure forming at the desired reaction temperature. The reaction time is generally from 1 to 8 h, preferably from 1 to 5 h.

Isolation of imidazolinone product (IV) can be achieved by standard methods. In a preferred embodiment water is added and organic solvents are distilled off. The residue can be taken up in water and acidified, whereupon compound (IV) precipitates. After filtration the crude product can be further purified, e.g. by stirring with water or recrystallization.

In a further embodiment of the invention there is provided a process for preparing herbicidal imidazolinones of formula (IV) comprising the step of (i) reacting compound (I) with a base selected from MOH and MOCH$_3$, where M is alkali metal, and (aqueous) H$_2$O$_2$ in methanol, optionally followed by acidification.

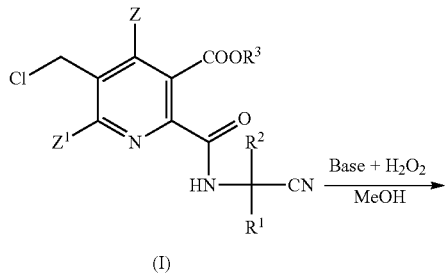

(I)

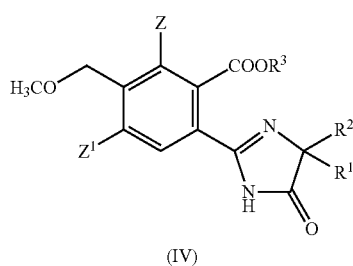

(IV)

The reaction may be carried out in analogy to the procedures described in EP-A 0 144 595.

EXAMPLES

The invention is illustrated by the following examples without limiting it thereby.

Example 1

Synthesis of 2-[(1-cyano-1,2-dimethylpropyl)carbamoyl]-5-chloromethyl nicotinic acid (Ia)

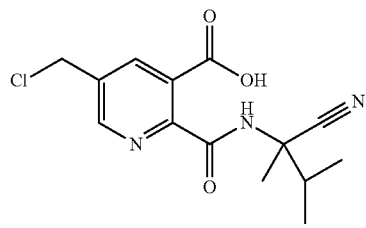 [SMILES: CC(C)C(C)(C#N)NC(=O)c1ncc(CCl)cc1C(=O)O]

9.6 g (48 mmol) 5-chloromethyl-pyridine-2,3-carboxylic acid anhydride (IIa), 40.0 g (435 mmol) toluene and 6.7 g (112 mmol) acetic acid were charged to a reactor and heated up to 69° C. 7.2 g (51 mmol) α-amino-1,2-dimethyl-butyronitrile were added over 25 min at a temperature between 72° C. and 76° C. The mixture was stirred for additional 90 min at 75° C. After cooling the mixture can be directly used for hydrolysis of the nitrile.

Example 2

Synthesis of Imazamox (IVa)

(a) Synthesis of 2-[(1-carbamoyl-1,2-dimethylpropyl)carbamoyl]-5-chloromethyl nicotinic acid (Va)

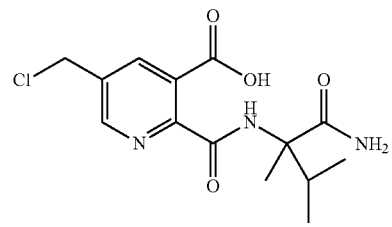 [SMILES: CC(C)C(C)(NC(=O)c1ncc(CCl)cc1C(=O)O)C(N)=O]

To 14.9 g (48 mmol) nitirile (Ia) (from example 1), 6.0 g (59 mmol) sulfuric acid (98%) was added at 69° C. to 80° C. within 5 min. 4.1 g (228 mmol) water was added at 70° C. to 78° C. and stirring continued at 69° C. for 5 h. The emerging product forms a toluene insoluble oil. The reaction mixture was used without workup in the following stage.

(b) Synthesis of Imazamox (IVa)

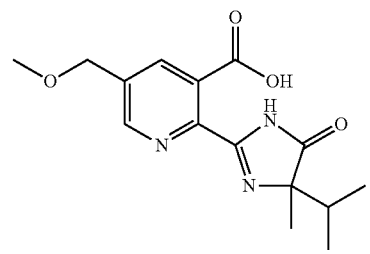 [SMILES: COCc1cnc(C2=NC(C)(C(C)C)C(=O)N2)c(C(=O)O)c1]

To 15.7 g (48 mmol) amido compound (Va) (reaction mixture from stage (a)) 94 g (2.94 mol) methanol was added at 65° C. and subsequently 42 g (525 mmol) NaOH (50% in water). The solution turned into a suspension, and stirring was continued for additional 90 min.

80 g water was added and solvents were removed at 50° C. and 80-8 mbar. Residue was dissolved in water and the basic solution acidified with 29 g sulfuric acid (98%). Imazamox precipitated from pH 4 on. The suspension was filtered at room temperature and washed with 100 ml water.

Yield: 16.5 g (82% pure, 44 mmol, 92%)

Purity was enhanced to >95% (HPLC) by stirring the crude product with water.

Example 3

Synthesis of 5-chloromethyl-2,3-pyridine dicarboxylic acid anhydride (IIa)

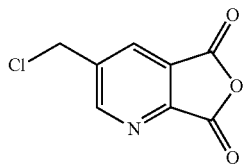

106.8 g (0.65 mol) of 5-methyl-2,3-pyridine dicarboxylic acid anhydride were dissolved in 427 g chlorobenzene and heated up to 85° C. A solution of 0.64 g (0.004 mol) AIBN in 99.0 g (0.66 mol) $SO_2Cl_2$ was added during 45 min. The mixture was stirred for additional 90 min at 85° C. Chlorobenzene was partly distilled off and the solution was cooled to 10° C. via 10 h ramp. The precipitate was filtered off and washed with chlorobenzene/hexane.

Yield: 85.0 g (0.40 mmol, 60%) of which 58.1 g (0.27 mmol) could be isolated after precipitation.

The invention claimed is:

1. A compound of formula (I),

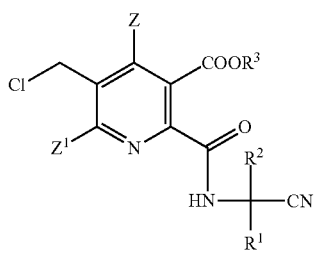

wherein
Z is hydrogen or halogen;
$Z^1$ is hydrogen, halogen, cyano or nitro;
$R^1$ is $C_1$-$C_4$ alkyl;
$R^2$ is $C_1$-$C_4$ alkyl or $C_3$-$C_6$ cycloalkyl or $R^1$ and $R^2$ together with the atom to which they are attached form a $C_3$-$C_6$ cycloalkyl group optionally substituted with methyl, and
$R^3$ is hydrogen or a cation.

2. The compound of claim 1, wherein Z and $Z^1$ are H.

3. The compound of claim 1, wherein
$R^1$ is $CH(CH_3)_2$ and
$R^2$ is $CH_3$.

4. The compound of claim 1, wherein
Z and $Z^1$ are H
$R^1$ is $CH(CH_3)_2$;
$R^2$ is $CH_3$ and
$R^3$ is H.

5. A process for preparing the compound of claim 1, comprising:

(i) reacting a compound of formula (II),

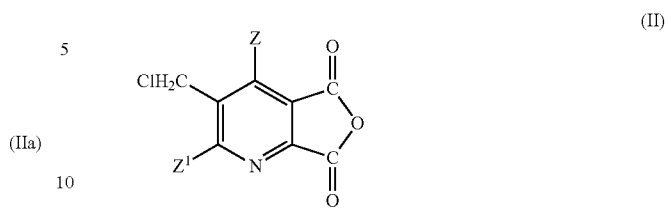

wherein,
with a 2-aminoalkane carbonitrile (III),

$$H_2N-CR^1R^2-CN \quad (III)$$

to obtain a compound of formula (I).

6. The process of claim 5, wherein the ratio of the compound formula of (II) to the compound of formula (III) is 1:0.8-1.2.

7. The process of claim 5, wherein said reacting of the compound of formula (II) with the compound of formula (III) is carried out in a solvent selected from the group consisting of aromatic hydrocarbons, chlorinated aromatic hydrocarbons, chlorinated aliphatic hydrocarbons, acetic acid, and mixtures thereof.

8. The process of claim 5, wherein either acetic acid is the solvent or 0.5 to 10 equivalents of acetic acid (based on (II)) are added to the solvent.

9. The process of claim 5, wherein the reaction is carried out at a temperature in the range of from 40 to 120° C.

10. The process of claim 5, wherein the reaction mixture is essentially free of pyridine, picolines and quinoline.

11. The process of claim 5, further comprising
(i-1) reacting a compound of formula (VI),

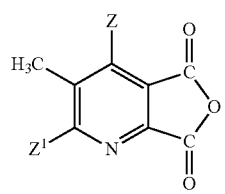

with a chlorinating agent, optionally in the presence of a radical initiator in a solvent selected from halogenated hydrocarbons, (i-2) crystallizing the compound (II) formed in step (i) from a solvent selected from the group consisting of 1,2-dichloroethane, chlorobenzene, 1,2-dichlorobenzene, 1,3-dichlorobenzene, 1,4-dichlorobenzene, trichloromethane, dichloromethane, toluene, xylenes, mesitylenes, alkyl acetates (e.g. ethyl acetate, butyl acetate, methyl acetate), methyl tert.-butyl ether, diisopropylether, cyclopentyl methyl ether, and mixtures thereof, to obtain anhydride (II), and (i-3) reacting anhydride (II) with a 2-aminoalkane carbonitrile (III),

$$H_2N-CR^1R^2-CN \quad (III)$$

to obtain a compound of formula (I).

12. A process for manufacturing an amide of formula (V),

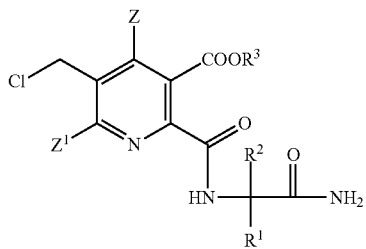
(V)

wherein
Z is hydrogen or halogen;
$Z^1$ is hydrogen, halogen, cyano or nitro;
$R^1$ is $C_1$-$C_4$ alkyl;
$R^2$ is s$C_1$-$C_4$ alkyl or $C_3$-$C_6$ cycloalkyl or $R^1$ and $R^2$ together with the atom to which they are attached form a $C_3$-$C_6$ cycloalkyl group optionally substituted with methyl, and
$R^3$ is hydrogen or a cation;
comprising
(i) hydrolyzing the compound of claim 1 to obtain an amide of formula (v).

13. A process for preparing a herbicidal imidazolinone compound of formula (IV),

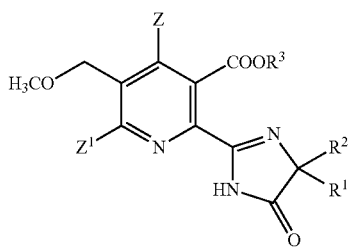
(IV)

wherein
Z is hydrogen or halogen;
$Z^1$ is hydrogen, halogen, cyano or nitro;
$R^1$ is $C_1$-$C_4$ alkyl;
$R^2$ is $C_1$-$C_4$ alkyl or $C_3$-$C_6$ cycloalkyl or $R^1$ and $R^2$ together with the atom to which they are attached form a $C_3$-$C_6$ cycloalkyl group optionally substituted with methyl, and
$R^3$ is hydrogen or a cation;
comprising
(i) hydrolyzing the compound of claim 1 to obtain an amide of formula (V), and
(ii) reacting compound (V) with $CH_3OM$ or $MOH/CH_3OH$ (where M is alkali metal), optionally followed by acidification to form the herbicidal imidazolinone (IV).

14. The process of claim 13, further comprising
(i-1) preparing the compound of formula (I) by reacting an anhydride of formula (II)

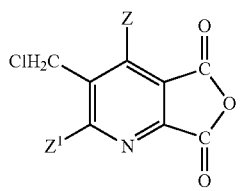
(II)

wherein
Z is hydrogen or halogen;
$Z^1$ is hydrogen, halogen, cyano or nitro;
with an aminonitrile (III)

$$H_2N-CR^1R^2-CN \qquad (III),$$

wherein
$R^1$ is $C_1$-$C_4$ alkyl;
$R^2$ is $C_1$-$C_4$ alkyl, $C_3$-$C_6$ cycloalkyl or $R^1$ and $R^2$ together with the atom to which they are attached form a $C_3$-$C_6$ cycloalkyl group optionally substituted with methyl and
(i-2) hydrolyzing the compound of formula (I) thus obtained to yield an amido compound of formula (V)

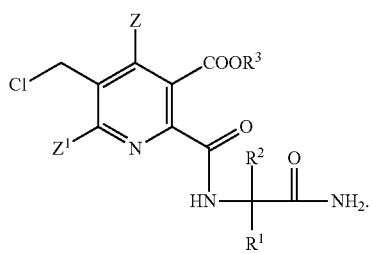
(V)

* * * * *